(12) United States Patent
Shidid et al.

(10) Patent No.: US 10,688,726 B2
(45) Date of Patent: Jun. 23, 2020

(54) METHOD FOR PRODUCING A CUSTOMISED ORTHOPAEDIC IMPLANT

(71) Applicant: Royal Melbourne Institute of Technology, Melbourne (AU)

(72) Inventors: Darpan Shidid, Jalgoan (IN); Martin Leary, Altona (AU); Milan Brandt, Templestowe (AU); Peter Choong, Kew (AU)

(73) Assignee: Royal Melbourne Institute of Technology, Melbourne, VIC (AU)

( * ) Notice: Subject to any disclaimer, the term of this patent is extended or adjusted under 35 U.S.C. 154(b) by 0 days.

(21) Appl. No.: 15/123,024

(22) PCT Filed: Mar. 4, 2015

(86) PCT No.: PCT/AU2015/000124
§ 371 (c)(1),
(2) Date: Sep. 1, 2016

(87) PCT Pub. No.: WO2015/131234
PCT Pub. Date: Sep. 11, 2015

(65) Prior Publication Data
US 2017/0071747 A1 Mar. 16, 2017

(30) Foreign Application Priority Data
Mar. 4, 2014 (AU) ................................. 2014900718

(51) Int. Cl.
| | |
|---|---|
| *B29C 67/04* | (2017.01) |
| *A61F 2/28* | (2006.01) |
| *B29C 64/393* | (2017.01) |
| *B33Y 10/00* | (2015.01) |
| *B29C 64/153* | (2017.01) |
| *A61F 2/30* | (2006.01) |
| *B29L 31/00* | (2006.01) |
| *B33Y 50/00* | (2015.01) |
| *B33Y 80/00* | (2015.01) |

(52) U.S. Cl.
CPC .............. *B29C 64/393* (2017.08); *A61F 2/28* (2013.01); *A61F 2/30942* (2013.01); *B29C 64/153* (2017.08); *B33Y 10/00* (2014.12); *A61F 2002/30006* (2013.01); *A61F 2002/30011* (2013.01); *A61F 2002/30014* (2013.01); *A61F 2002/3092* (2013.01); *A61F 2002/3093* (2013.01); *A61F 2002/3097* (2013.01); *A61F 2002/30263* (2013.01); *A61F 2002/30948* (2013.01); *A61F 2002/30952* (2013.01); *A61F 2002/30962* (2013.01); *A61F 2002/30985* (2013.01); *A61F 2240/002* (2013.01); *B29L 2031/7532* (2013.01); *B33Y 50/00* (2014.12); *B33Y 80/00* (2014.12)

(58) Field of Classification Search
CPC .......................... B29C 64/153; B29C 64/393
See application file for complete search history.

(56) References Cited

U.S. PATENT DOCUMENTS

| | | | | |
|---|---|---|---|---|
| 5,370,692 A | * | 12/1994 | Fink ........................ | B29C 41/36 |
| | | | | 128/898 |
| 5,690,490 A | | 11/1997 | Cannon | |
| 5,741,215 A | | 4/1998 | D'Urso | |
| 5,798,924 A | | 8/1998 | Eufinger | |
| 6,932,842 B1 | * | 8/2005 | Litschko ................... | A61F 2/30 |
| | | | | 623/16.11 |
| 8,430,930 B2 | * | 4/2013 | Hunt ......................... | A61F 2/28 |
| | | | | 623/17.11 |
| 8,457,930 B2 | * | 6/2013 | Schroeder ................. | A61F 2/30 |
| | | | | 703/1 |

(Continued)

FOREIGN PATENT DOCUMENTS

| | | |
|---|---|---|
| CA | 2373691 | 11/2000 |
| CN | 1350667 A | 5/2002 |

(Continued)

OTHER PUBLICATIONS

Castells, Ryan; DMLS vs SLM 3D Printing for Metal Manufacturing; Retrieved from https://www.element.com/nucleus/2016/06/29/dmls-vs-slm-3d-printing-for-metal-manufacturing on Jul. 29, 2019; Updated on Jun. 29, 2016. (Year: 2016).*
Yap et al.; Review of selective laser melting: Materials and applications; Appl. Phys. Rev. 2, 041101 pp. 1-21; 2015. (Year: 2015).*
International Search Report, PCT/AU2015/000124 filed Mar. 4, 2015.
Docquier, Pierre-Louis, et al. "Computer-assisted resection and reconstruction of pelvic tumor sarcoma." Sarcoma 2010 (2010).
Unwin, Paul. "Fabricating specialised orthopaedic implants using additive manufacturing." SPIE LASE. International Society for Optics and Photonics, 2014.
China Patent Office, First Office Action, dated Sep. 18, 2017.
European Patent Office, Search Report, dated Oct. 26, 2017.

(Continued)

*Primary Examiner* — Atul P. Khare

(74) *Attorney, Agent, or Firm* — Dority & Manning, P.A.

(57) ABSTRACT

A method for producing a customised orthopaedic implant is provided. The method involves scanning a bone from which a diseased region of bone will be resected to obtain a three dimensional digital image of an unresected volume of bone; scanning the bone after a diseased region of bone has been resected to obtain a corresponding three dimensional digital image of a resected volume of bone; and comparing the three dimensional digital image of the unresected volume of bone to the corresponding three dimensional digital image of the resected volume of bone to estimate a volume of bone that has been resected. The estimate of the volume of bone that has been resected is used to design a customised orthopaedic implant that substantially corresponds to the configuration of the resected volume of bone, the implant being configured to substantially restore a biomechanical function of the bone. Finally the customised orthopaedic implant is manufactured and provided for insertion into the resected region of bone.

10 Claims, 13 Drawing Sheets

(56) References Cited

U.S. PATENT DOCUMENTS

| | | | | |
|---|---|---|---|---|
| 8,485,820 B1* | 7/2013 | Ali | ............... | A61C 8/0027 433/173 |
| 8,556,981 B2* | 10/2013 | Jones | ............... | A61F 2/30907 623/18.11 |
| 8,700,198 B2* | 4/2014 | Conway | ............... | A61B 17/8066 606/109 |
| 8,775,133 B2* | 7/2014 | Schroeder | ............... | A61F 2/30 703/1 |
| 8,888,485 B2* | 11/2014 | Ali | ............... | A61C 8/0027 433/173 |
| 8,926,707 B2* | 1/2015 | McMinn | ............... | A61F 2/3603 623/23.14 |
| 8,974,535 B2* | 3/2015 | Antonyshyn | ............... | A61F 2/2875 623/17.18 |
| 9,764,510 B2* | 9/2017 | Antonyshyn | ............... | A61F 2/2875 |
| 2007/0118243 A1* | 5/2007 | Schroeder | ............... | B33Y 50/00 700/118 |
| 2009/0076508 A1 | 3/2009 | Weinans et al. | | |
| 2011/0144752 A1* | 6/2011 | Defelice | ............... | A61F 2/28 623/16.11 |
| 2012/0010711 A1* | 1/2012 | Antonyshyn | ............... | A61F 2/2875 623/16.11 |
| 2012/0319332 A1* | 12/2012 | Mcminn | ............... | A61F 2/30771 264/494 |
| 2013/0060347 A1 | 3/2013 | McMinn | | |
| 2013/0204384 A1* | 8/2013 | Hensley | ............... | A61F 2/30942 623/20.35 |
| 2015/0224226 A1* | 8/2015 | Bhatia | ............... | C12N 5/0068 435/1.1 |

FOREIGN PATENT DOCUMENTS

| | | |
|---|---|---|
| CN | 102946827 A | 5/2009 |
| CN | 101431966 A | 2/2013 |
| WO | WO2007053022 | 5/2007 |
| WO | WO2011131927 | 10/2011 |

OTHER PUBLICATIONS

*Orthopedics of Mechanics of Biomaterials: Fundamental Principles for Implant Design*, Cambridge University Press (2011): Chapter 13.

1$^{st}$ Examination Report issued by IP Australia dated Nov. 16, 2018.

3$^{rd}$ Office Action issued by the State Intellectual Property Office of China (SIPO) dated Mar. 4, 2019.

* cited by examiner

METHOD FOR PRODUCING A CUSTOMISED ORTHOPAEDIC IMPLANT

TECHNICAL FIELD

The present invention relates to methods for designing and manufacturing customised orthopaedic implants. More particularly, the method relates to design and production of patient-specific orthopaedic implants for insertion into a resected region of bone.

BACKGROUND OF INVENTION

Osteosarcomas are a class of cancer originating from the bone, mainly affecting children or young adults. Prior to the 1970s, amputation was the sole means of treatment available. Amputation results in poor outcomes for patients in terms of quality of life and accordingly current trends are directed toward trying to salvage the affected limb while resecting the tumour in its entirety to reduce the risk of local recurrence and to maximise the prospects of survival. Once the tumour is resected, further surgery is typically required to reconstruct the limb.

Efforts to salvage the limb often involve the insertion of orthopaedic implants to reconstruct the bone or replacement of natural joints with prosthesis. Conventional orthopaedic implants generally have a solid construction intended to structurally stabilise the resected bone to which they are attached. To stabilise small tumour resections, solid metallic plate type implants may be fixed to the bone tissue using multiple screws. These implants are available in standard shapes and sizes and the surgeon usually adjusts the implant contour to align with the bone during surgery using trial and error. For tumours located near joints, a total joint replacement prosthesis is used. These implants are substantial in design to improve fatigue life and accordingly require significant removal of bone tissue from the affected as well as the unaffected region to accommodate the prosthesis. In the case of young patients whose bones have not matured, an expandable prosthesis may be used requiring repeat visits to biomechanics laboratories for lengthening. Once the bones reach maturity the expandable prosthesis is replaced with permanent joint replacement prosthesis, resulting in further surgery and rehabilitation for the patient. For elderly patients, the chances of prosthesis failure are greater, due to reduced physical activity and other age related complications such as osteoporosis. Moreover, the placement strategy for such prosthesis tends to focus on the configuration of the standard orthopaedic implant and how the existing bone needs to be shaped to conform to the implant, rather than focusing on the anatomical function of the bone and what is required to maintain optimal biomechanical function of the limb.

The disparity in stiffness between the existing bone and the orthopaedic implant can lead to bone resorption and subsequent loosening of the orthopaedic implant. While in some cases, conventional orthopaedic implants do provide a satisfactory result that allow the patient to return to an active lifestyle, in others, use conventional orthopaedic implants has resulted in extended rehabilitation, pain, discomfort, and lack of mobility. Therefore, there is need for the development of customised orthopaedic implants that are optimised to loading conditions of the affected region, are affordable and can be rapidly produced.

It would therefore be desirable to be able to design and manufacture an orthopaedic implant which is customised for a patient and specific to a diseased skeletal element. In particular, it would be desirable to be able to automate design of orthopaedic implants which offer a suitable compromise to the bone's inherent biomechanical function and enhance bone in-growth rate. Finally, it would be desirable to optimise the entire process of designing and manufacturing customised orthopaedic implants to enable orthopaedic implant design, manufacture and placement to take place within the time constraints of surgery.

SUMMARY OF INVENTION

According to an aspect of the present invention, there is provided a method for producing a customised orthopaedic implant, the method including the following steps: (a) scanning a bone from which a diseased region of bone will be resected to obtain a three dimensional digital image of an unresected volume of bone; (b) scanning the bone after a diseased region of bone has been resected to obtain a corresponding three dimensional digital image of a resected volume of bone; (c) comparing the three dimensional digital image of the unresected volume of bone to the corresponding three dimensional digital image of the resected volume of bone to estimate a volume of bone that has been resected; (d) using the estimate of the volume of bone that has been resected to design a customised orthopaedic implant that substantially corresponds to a configuration of the resected volume of bone, the implant being configured to substantially restore a biomechanical function of the bone; (e) manufacturing the customised orthopaedic implant; and (f) providing the customised orthopaedic implant for insertion into the resected region of bone.

Design of the customised orthopaedic implant to substantially restore the biomechanical function of the bone involves consideration of one or more typical loading conditions on a bone type which corresponds to the bone that has been resected. For instance, this may involve a consideration of the anatomical function of the bone type in question and the anticipated bone loading during various typical activities.

Design of the customised orthopaedic implant preferably involves consideration of typical maximum stress and deflection to which the bone type which corresponds to the resected bone is subjected. That is, taking into account the physique of the patient, the loads incurred by the bone type during typical activities such as walking, running, jumping and external impact can be modelled.

In a particular embodiment, the customised orthopaedic implant includes a lattice-type geometry. The density of the lattice-type geometry is configured to enhance bone ingrowth and is optimised to neutralise stresses developed at the bone-implant interface. The lattice-type geometry is preferable since it offers a favourable strength to weight ratio, reduces stress shielding and can be manufactured using additive technology. In a more particular embodiment, the lattice-type geometry includes a periodic arrangement. Such an arrangement provides more predictable mechanical properties and behaviour and accordingly, provides greater control over the ultimate performance of the customised orthopaedic implant in-situ. That is, varying the porosity of the lattice structure at a bone/implant interface can be used to enhance bone ingrowth or increase implant stiffness.

The customised orthopaedic implant is preferably manufactured using additive manufacturing technology. The additive manufacturing technology may involve selective laser melting.

In one form of the invention, scanning a bone to obtain a three dimensional digital image involves obtaining a plurality of two dimensional digital images and constructing a three dimensional digital image therefrom.

Each three dimensional digital image may comprise a stereo lithography file (STL).

Scanning the bone to obtain one or more three dimensional digital images may involve the use of a medical imaging such as computed tomography (CT) scanner and Magnetic Resonance Imaging (MRI). Alternately, scanning the bone to obtain one or more digital images may involve use of a laser scanner.

Preferably, the three dimensional digital image is used to generate a three dimensional computer model of the customised orthopaedic lattice implant. The three dimensional computer model is subsequently transmitted to a three dimensional printer.

In one particular embodiment, the diseased region of bone is affected by osteosarcoma.

In a preferred form of the invention, the steps of the method for producing a customised orthopaedic implant occur consecutively during a period of time in which the patient is under anaesthesia.

According to another aspect of the present invention, there is provided a customised orthopaedic implant, the implant formed by a method including the following steps: scanning a bone from which a diseased region of bone will be resected to obtain a three dimensional digital image of an unresected volume of bone; scanning the bone after which a diseased region of bone has been resected to obtain a corresponding three dimensional digital image of a resected volume of bone; comparing the three dimensional digital image of the unresected volume of bone to the corresponding three dimensional digital image of the resected volume of bone to estimate a volume of bone that has been resected; using the estimate of the volume of bone that has been resected to design a customised orthopaedic implant substantially corresponding to a configuration of the resected volume of bone, the implant being configured to substantially restore the biomechanical function of the bone; and manufacturing the customised orthopaedic implant.

BRIEF DESCRIPTION OF DRAWINGS

The invention will now be described in further detail by reference to the accompanying drawings. It is to be understood that the particularity of the drawings does not supersede the generality of the preceding description of the invention.

DETAILED DESCRIPTION

Figure 1:
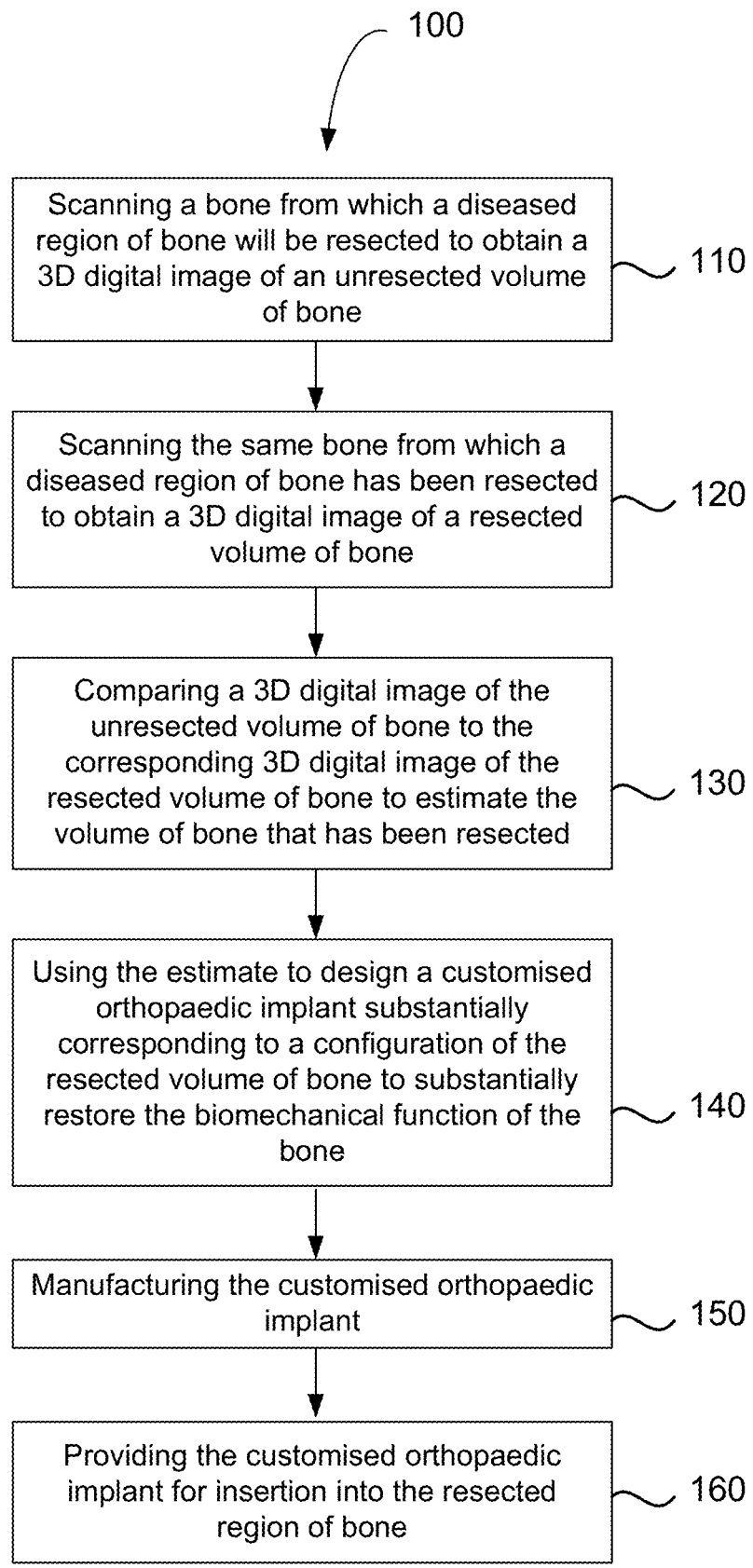
FIG. 1 is a flowchart showing the method for producing a customised orthopaedic implant according to an embodiment.

Referring firstly to FIG. 1, there is shown a flowchart illustrating the method 100 for producing a customised orthopaedic implant. At step 110, a bone from which a diseased region of bone will be resected is scanned to obtain a three dimensional digital image of an unresected volume of bone. At step 120, the same bone from which a diseased region of bone has been resected is scanned to obtain a three dimensional digital image of a resected volume of bone. At step 130, a three dimensional digital image of the unresected volume of bone is compared to the corresponding three dimensional digital image of the resected volume of bone to estimate the volume of bone that has been resected. At step 140, the estimate of the volume of bone that has been resected is used to design a customised orthopaedic implant which substantially corresponds to a configuration of the resected volume of bone. Modelling is performed to ensure proposed customised orthopaedic implant should substantially restore the biomechanical function of the bone. At step 150, the customised orthopaedic implant is manufactured. Finally, at step 160, the customised orthopaedic implant is provided for insertion into the resected region of bone.

It is to be understood that the steps of the method take place while the respective patient is in surgery and generally under anaesthesia. Moreover, the invention is herein described in the context of designing and manufacturing orthopaedic implants to replace sections of tissue surgically resected to remove an osteosarcoma. However, it is to be understood that the method of producing customised orthopaedic implants may have broader application than that in the context of which the invention is herein described.

Manufacture of customised implants within surgical time constraints can be achieved using additive or three dimensional printing techniques as subsequently described.

Figure 2A:
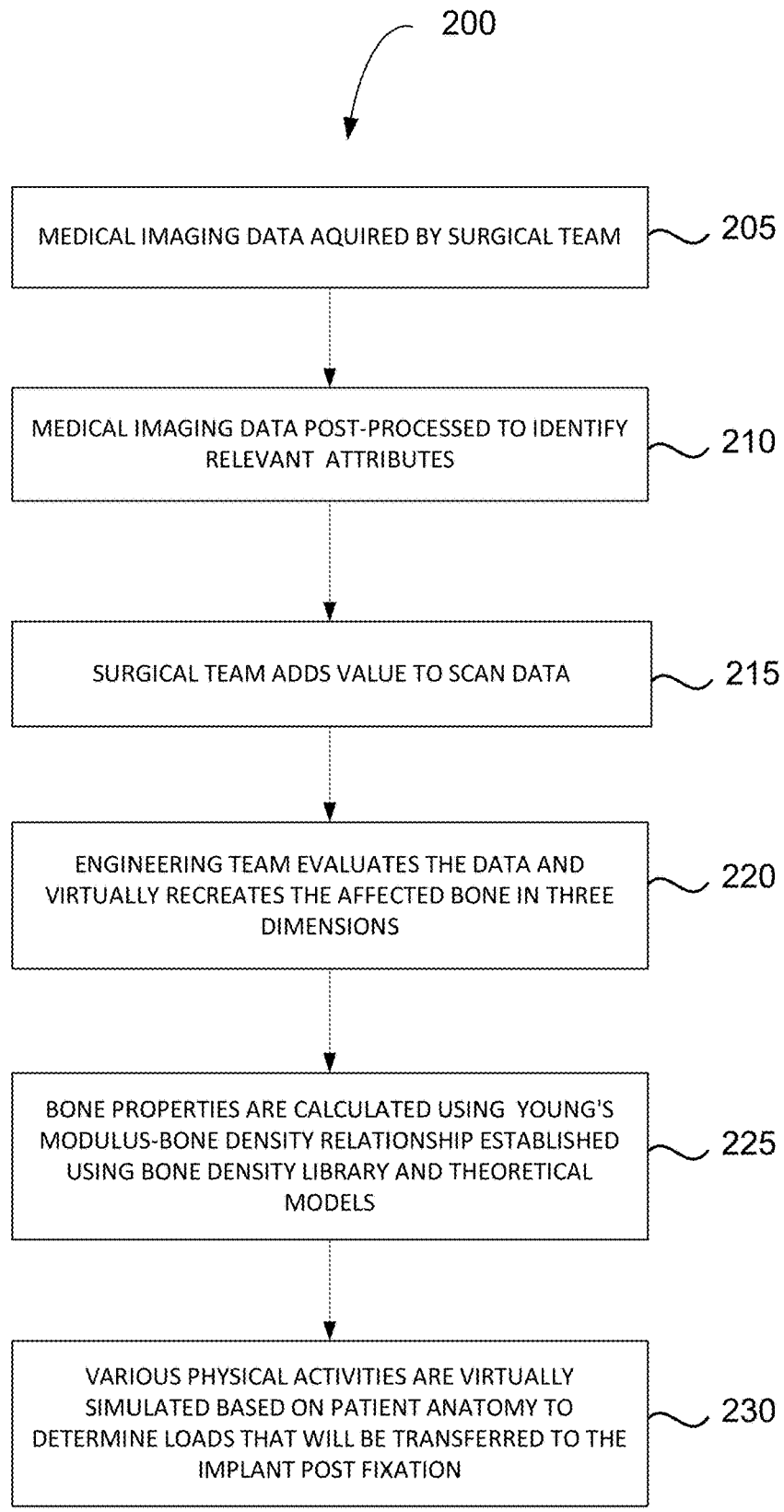
FIGS. 2A to 2C show a more detailed flowchart showing the method for producing a customised orthopaedic implant.

The method will now be described in more detail with reference to the flowchart provided in FIGS. 2A to 2C. Referring now to FIG. 2A, at step 205, the surgical team acquires medical imaging data of the disease affected bone by scanning the bone using, for example, a laser or computed tomography (CT) scanner. Imaging a bone to obtain three dimensional models requires obtaining a plurality of two dimensional digital images and constructing a three dimensional digital image therefrom. Once scanning is complete, at step 210, the medical imaging data is processed in order to identify relevant features and attributes of the instant bone such as the anatomical position of the osteosarcoma within the bone, and the shape and size of the osteosarcoma. At step 215, the surgical team examines the medical imaging data of the diseased bone, as shown for example in FIG. 3A, to determine the region of bone to be resected to remove the osteosarcoma, using a three dimensional comparison of diseased and normal bone as shown for example in FIG. 3B. At this stage, the surgical team determines how the customised orthopaedic implant will be fixed to the bone, so that the preferred fixation strategy can be taken into account during orthopaedic implant design. Surgical data, as shown in FIG. 3C, is sent to the engineering team in real-time during the surgical procedure.

At step 220 the processed scan data is reviewed by an engineering team and the orthopaedic implant design process commences. The medical image data files typically comprise CT scan data that are converted into three dimensional stereo lithography (STL) files as shown for example in FIG. 3A. The STL files of the resected volume of bone can be imported directly into the design algorithm, avoiding any requirement for decimation of medical imaging data or the use of finite element mesh creation software. This ultimately results in enhanced optimal geometric integrity of the customised implant and a more precise fit.

Figure 4B:
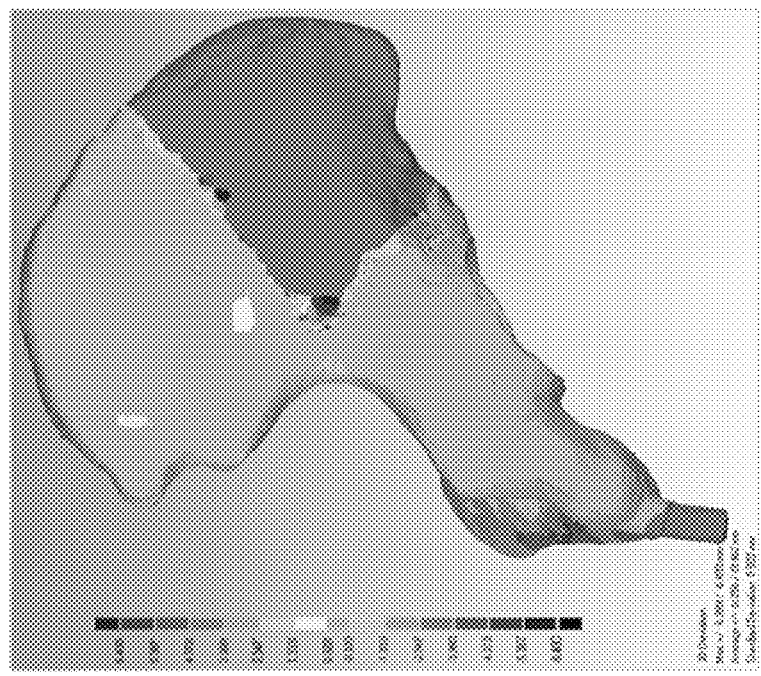
FIGS. 4A and 4B show the output of two different STL file comparisons to estimate the amount of tissue removed from diseased bone of different bone types.
Figure 4A:
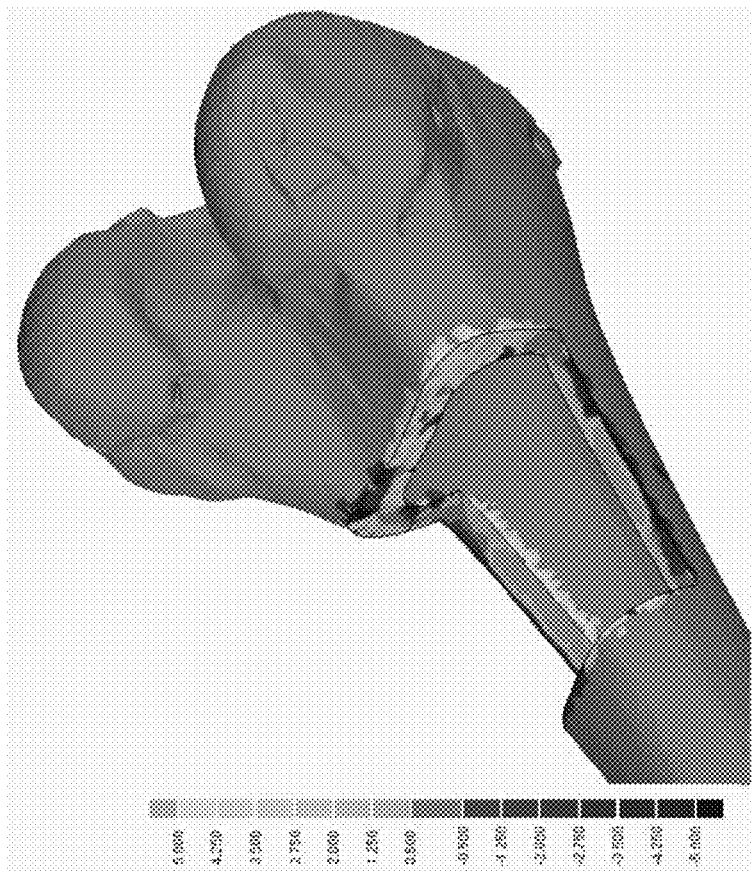

The resulting virtual three dimensional model is used compare models of the unresected volume of bone with the models of the resected volume of bone to provide an estimate of the volume of bone that will be resected as shown for example in FIGS. 4A and 4B.

Figure 5C:
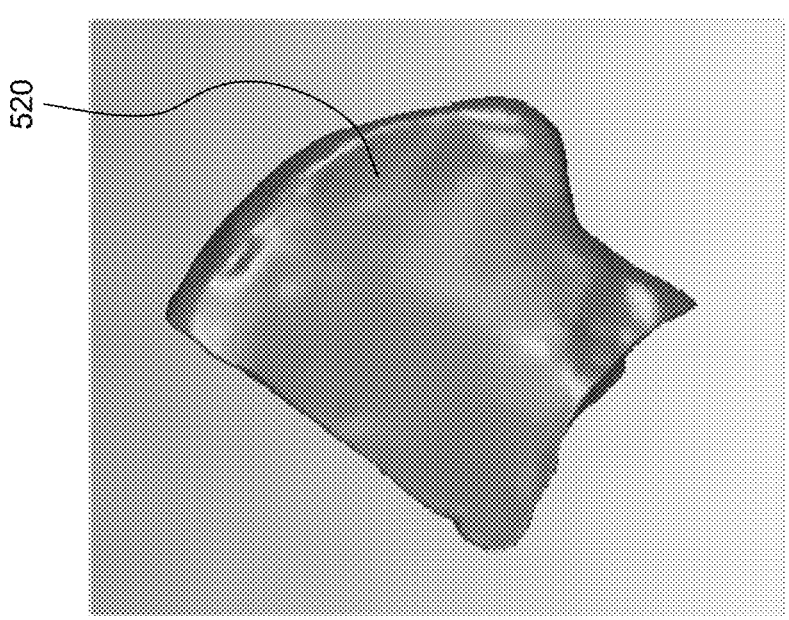
FIGS. 5A to 5C show stepwise rendering of customised orthopaedic implant to replace the amount of tissue removed from the diseased bone shown in FIGS. 4B and 5A.
Figure 5B:
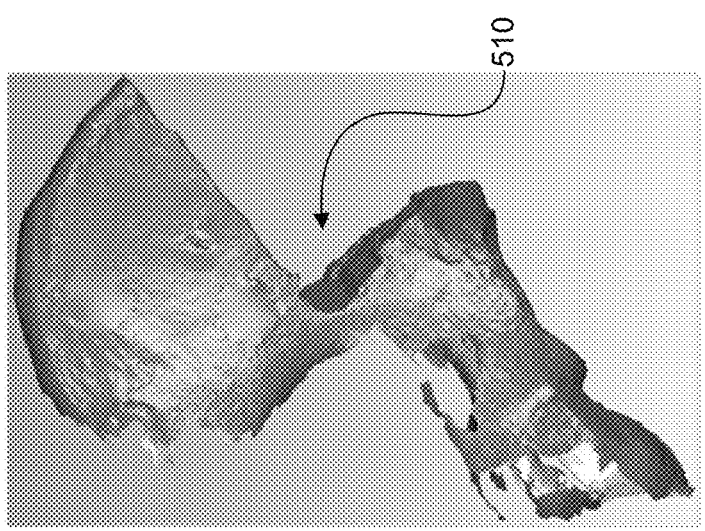
Figure 5A:
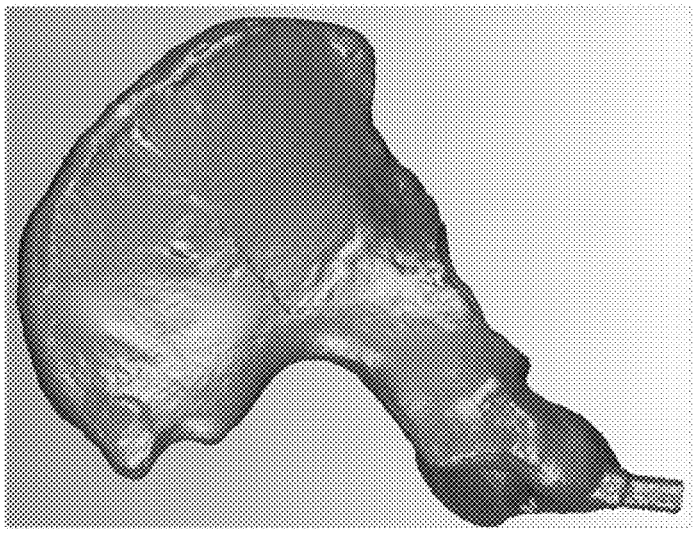

FIGS. 5A to 5C further illustrate how the STL files can be used to model the amount of tissue to be resected 510, as shown in FIG. 5B. The resected region of bone 510 is then precisely filled using CAD modelling constrained by the preresection medical image data to provide a generalised shape of the proposed orthopaedic implant 520 as shown in FIG. 5C.

Since the aim of limb salvage surgery is to fill the resected region with a customised orthopaedic implant which substantially corresponds to not only to the configuration of the resected volume of bone, but also to ensure that the orthopaedic implant substantially corresponds to the biomechanical properties of the surrounding bone, the orthopaedic implant design must take into account the properties of the surrounding bone. These properties can be calculated using Young's Modulus-bone density relationship using a bone density library and well established theoretical models at step 225.

Use of high resolution STL files enables accurate assignment of patient specific loads and boundary conditions such as tendon and ligament attachments that can be discerned from medical imaging data. The patient specific loads and boundary conditions are typically ascertained from magnetic resonance imaging (MRI) data or similar, whilst the resected bone volume determinations may be based on computed tomography (CT) data, laser scanner or the like.

At step 230, a variety of physical activities and movements are simulated whilst taking into account the patient's age and physique, i.e. height, weight etc., in order to determine the loads that will be incurred by the customised orthopaedic implant post fixation. Such activities may include walking, running, jumping and external impact. Each activity will subject the orthopaedic implant to different load magnitudes and directions.

Figure 6A:
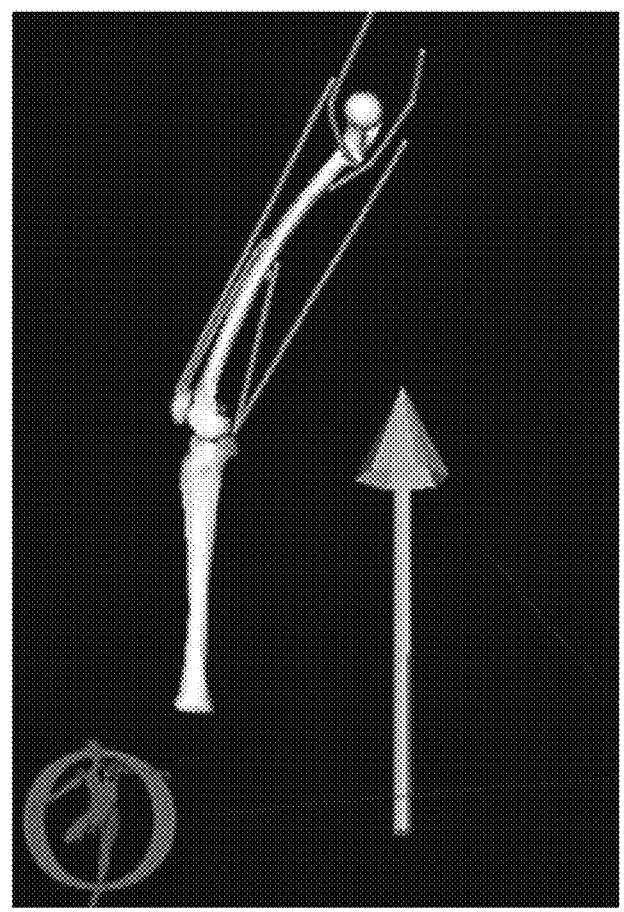
FIGS. 6A and 6B are schematic representations showing determination of loads and stresses incurred by a resected femur during walking.
Figure 6B:
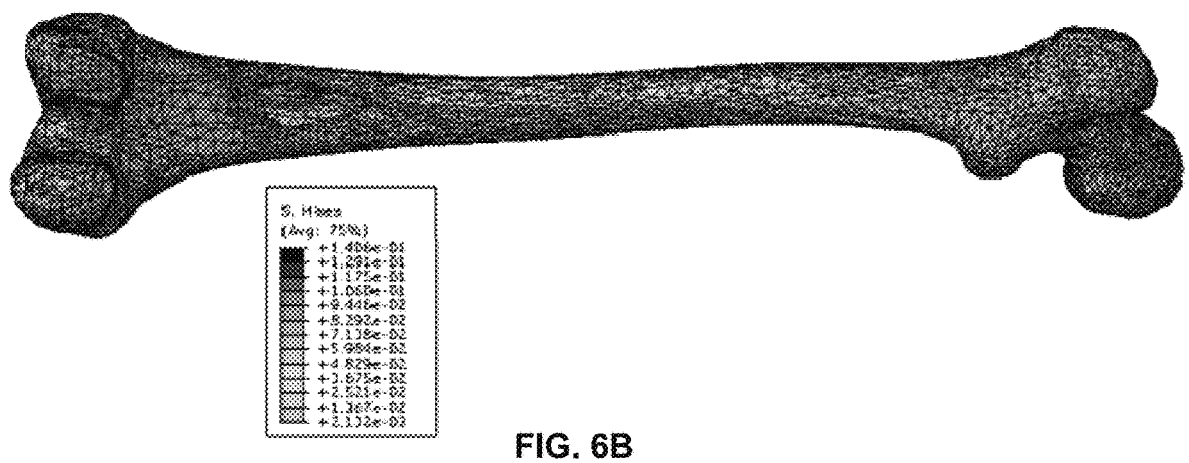

An example of a simulation is shown in FIG. 6A, wherein the loads on a femur whilst walking are illustrated. These loads may be estimated using OpenSim software tool (Delp S L, Anderson F C, Arnold A S, Loan P, Habib A, John C T, Guendelman E, Thelen D G. OpenSim: Open-source Software to Create and Analyze Dynamic Simulations of Movement. IEEE Transactions on Biomedical Engineering. (2007)) or similar. The estimated loads are applied to a three dimensional model of the femur to illustrate the loads on different areas of the femur as shown in FIG. 6B. Different activities will subject the orthopaedic implant to different load magnitudes and directions dependent on the physique of the patient.

Figure 2B:
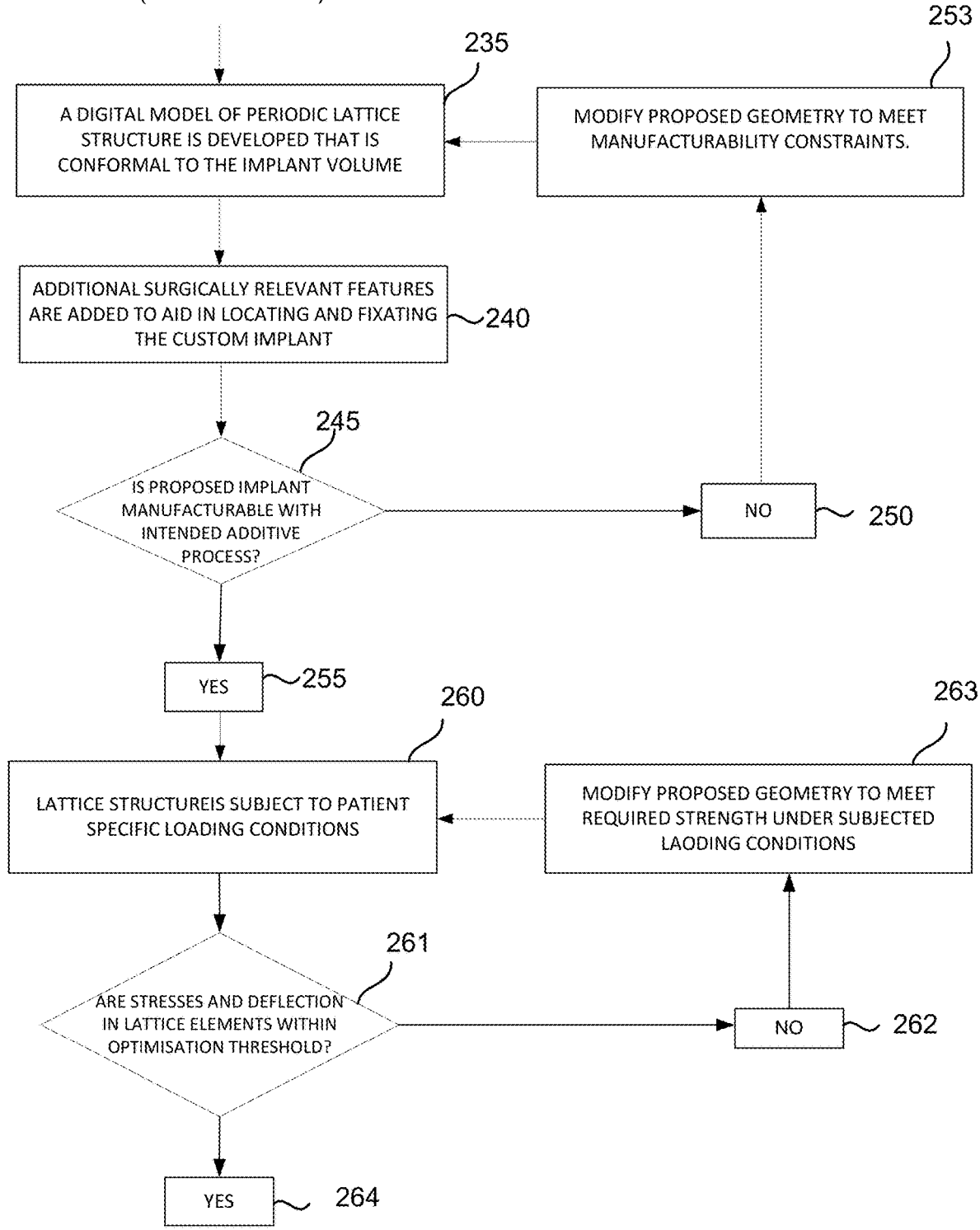
Figure 2C:
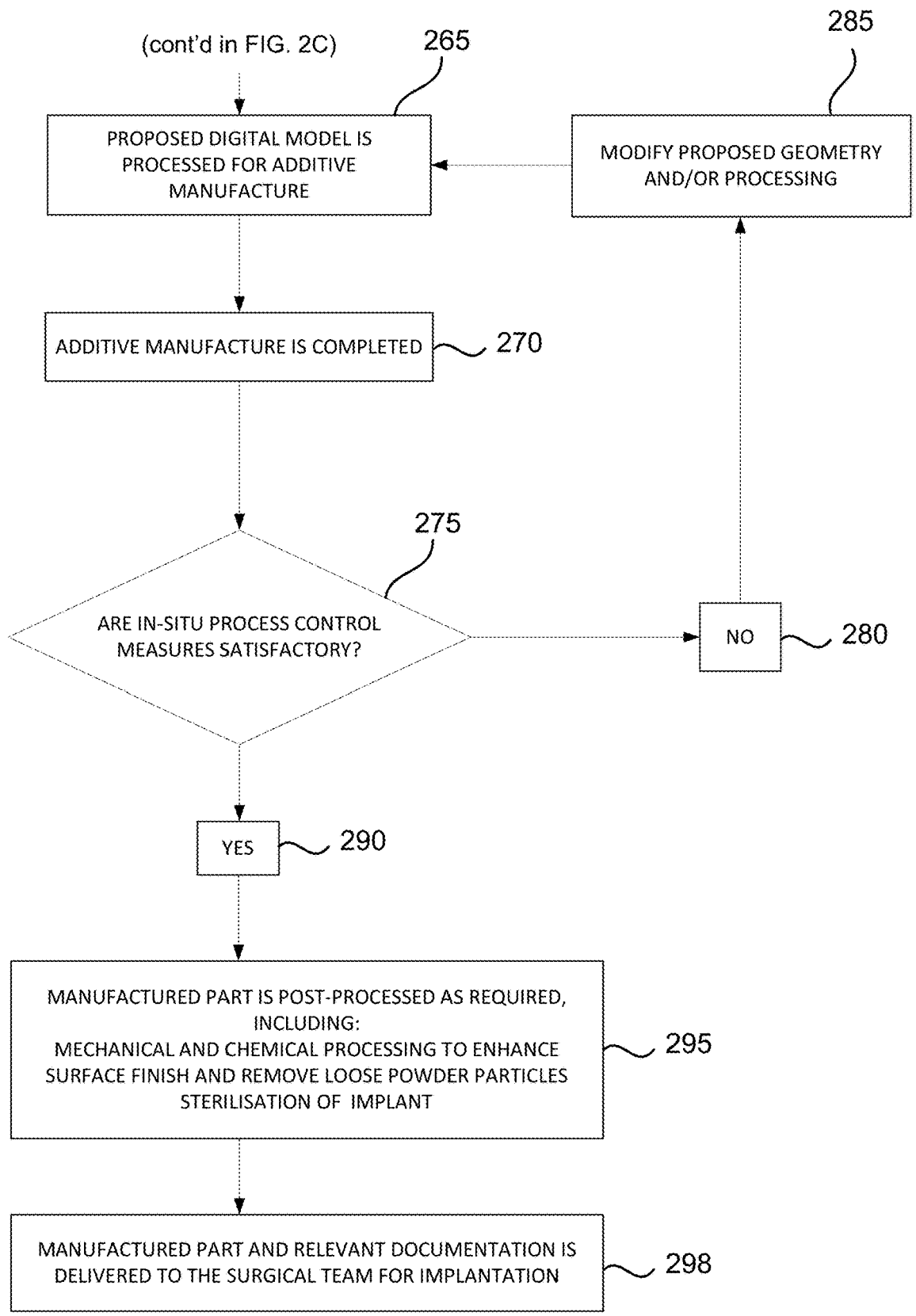
Figure 3C:
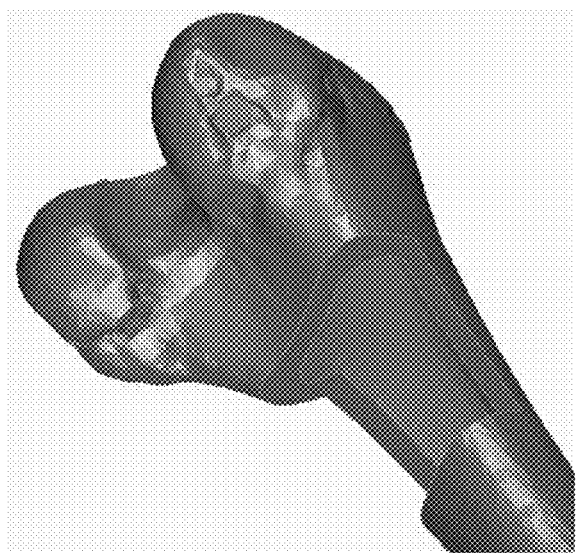
FIG. 3C shows the diseased bone of FIG. 3A with osteosarcoma tissue removed.
Figure 3B:
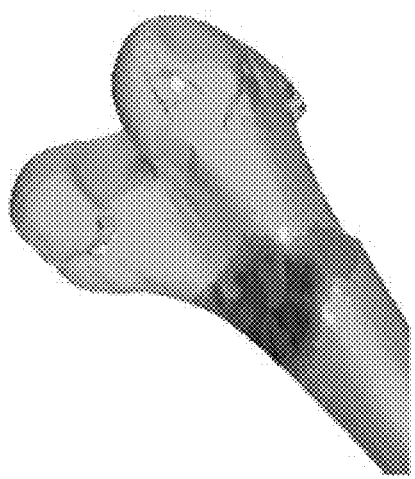
FIG. 3B is shows a 3D comparison between the diseased bone and a normal bone to assist in surgical planning.
Figure 3A:
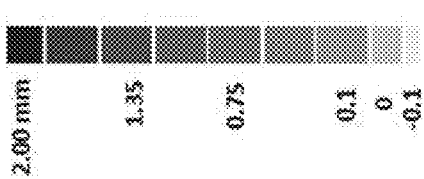
FIG. 3A is a schematic of a diseased bone showing the amount of tissue to be removed.
Figure 3A:
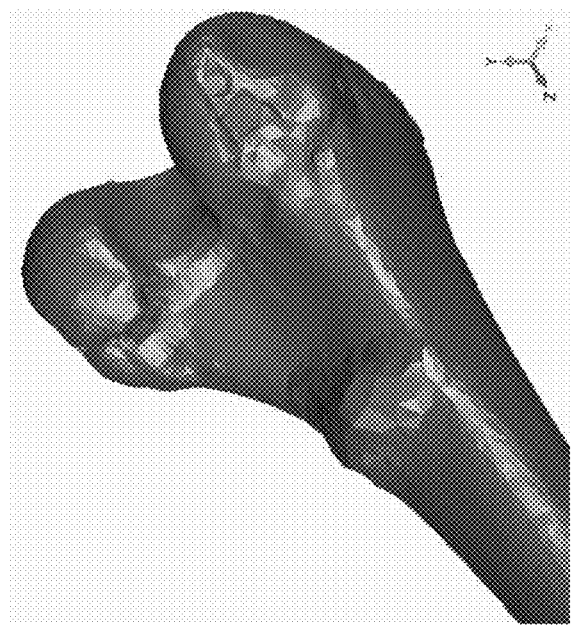

Referring now to FIG. 2B, a digital model of the orthopaedic implant comprising of lattice structure that is conformal to the resected volume of the bone is developed at step 235. This step is carried out using a custom designed algorithm, which automatically imports the implant volume and converts it into a periodic lattice structure. At this stage features such as density gradient, choice of unit cell are interactively selected via a graphic user interface (GUI).

At step 240, the resulting digital model of the customised orthopaedic implant is adjusted to accommodate the requisite surgical features that are necessary to enable the orthopaedic implant to be suitably located and fixed to the bone. Such surgical features include custom surgical guides, fixation brackets and tailored screws.

Later at step 245, the proposed orthopaedic implant configuration is assessed to determine whether it can be manufactured using additive technology. Typical additively manufactured parts use structural supports to brace the part against the loads generated while laying and solidifying the preceding layers. These structures are difficult to remove, especially for complex geometries such as lattice structures. Hence it is desirable to avoid use of support structures within the part. If the proposed orthopaedic implant is not able to be manufactured without the use of support structures, using additive technology at 250, then the proposed orthopaedic implant configuration is modified to meet the manufacturing constraints at step 253. Some examples of suitable modifications include changing a feature thickness, modifying an inclination of a feature, adding or removing support features. Residual stresses owing to the thermal gradient between the lattice and fixation brackets are compensated by generating additional removable struts.

Development and optimisation of the digital implant model takes into account the anatomical function of the bone, the properties of the bone, e.g. density gradient and corresponding variation in stiffness, and the anticipated load that the orthopaedic implant will be subject to during typical activities and movements.

Figure 7B:
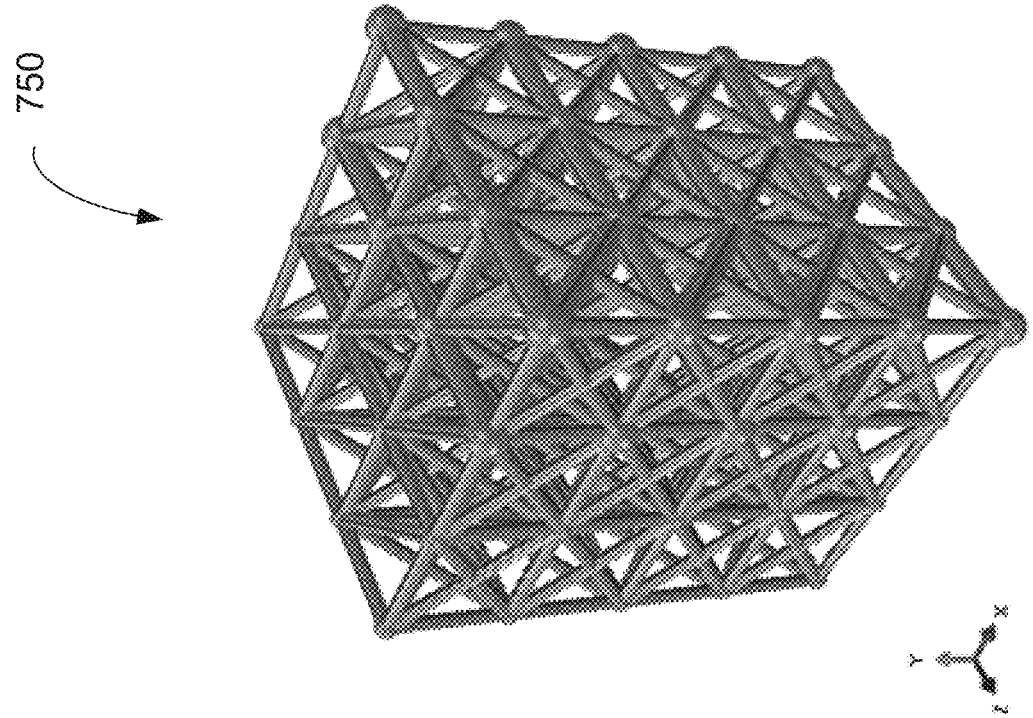
FIG. 7B shows a lattice structure which is optimised for the loading conditions and further optimised for manufacture using additive manufacturing processes.
Figure 7A:
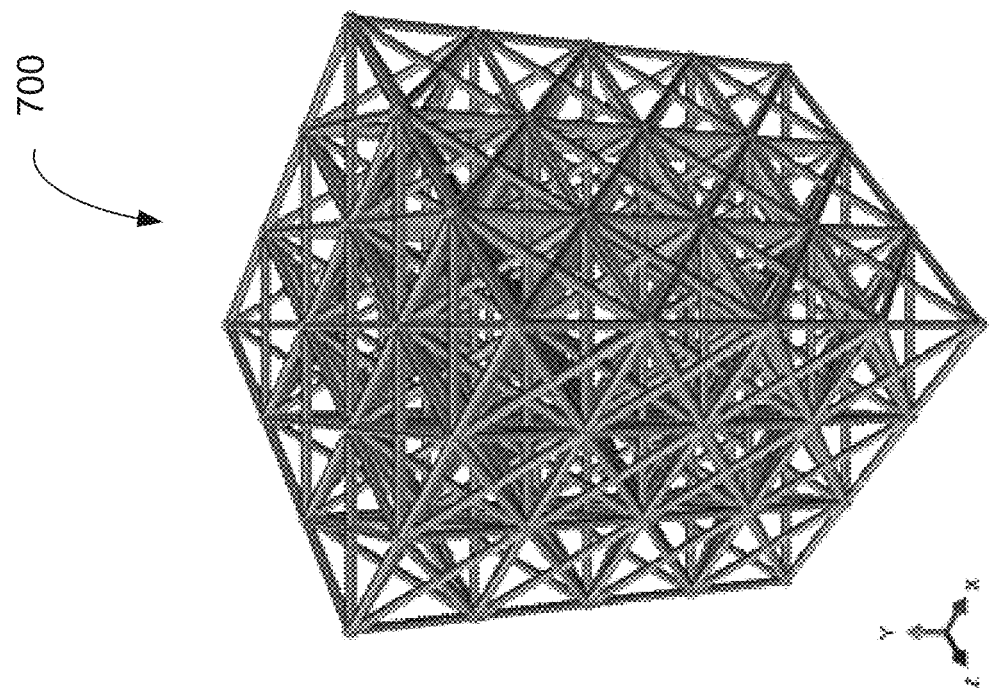
FIG. 7A shows example of a lattice structure which is optimised for the loading conditions, but is not manufacturable using additive manufacturing.

Once the manufacturability of the implant is ensured at step 255, the lattice geometry or truss structure 700, 750 as generally shown in FIGS. 7A and 7B can be automatically optimised to take specified stresses, deflections and loading conditions as determined at step 230

The lattice structure 750 shown in FIG. 7B is optimised to neutralise all possible forms of loading conditions and transmit the load to the load bearing bone and lends itself to manufacturing by additive technology. The lattice structure 700 shown FIG. 7A shows example of an optimised lattice structure that is not manufacturable using additive manufacturing and accordingly not suitable for rapid manufacture of customised orthopaedic implants within surgical time constraints.

A lattice structure with a periodic arrangement is preferred, i.e. a periodic layout of nodes and struts, since it results in predictable mechanical properties and behaviour. A periodic arrangement enables utilisation of a unit cell based topology wherein the user can assign different types of unit cells according to the structural requirements of the implant. An example of such a periodic lattice structure 800 is shown in FIG. 8A.

In contrast, aperiodic structures have non-organised arrangement of struts and nodes, making prediction of mechanical behaviour difficult. Currently, two strategies are employed to generate conformal lattice structures. Using the most common method, the organic volume to be filled is intersected by a periodic arrangement of lattice unit cells. Due to periodic nature of the lattice structure and aperiodic surface contour, intersection of lattice structure at nodes is not guaranteed. Accordingly, the structural integrity of such structures is compromised and the purpose of using a periodic structure is not fulfilled. Such structures are also difficult to optimise using available optimisation tools. Using another method of generating conformal lattice structures, the organically shaped volume is decimated using STL processing software and the corresponding arrangement of nodes and vertices is converted into a lattice structure. Due to aperiodic placement of triangles on a STL file, the resulting structure is also aperiodic. Furthermore, as a result of shape deformation during decimation, accurate application of muscle loads and boundary conditions is difficult. The presently proposed algorithm takes into account the potential shortcomings and aforementioned issues. The ensuing lattice structure is generated directly from a high resolution STL file, enabling accurate assignment of loading conditions. Furthermore, all nodes are located on the surface of the STL, ensuring that the loads are applied at nodes and optimisation process for such structure is computationally efficient.

Figure 8A:
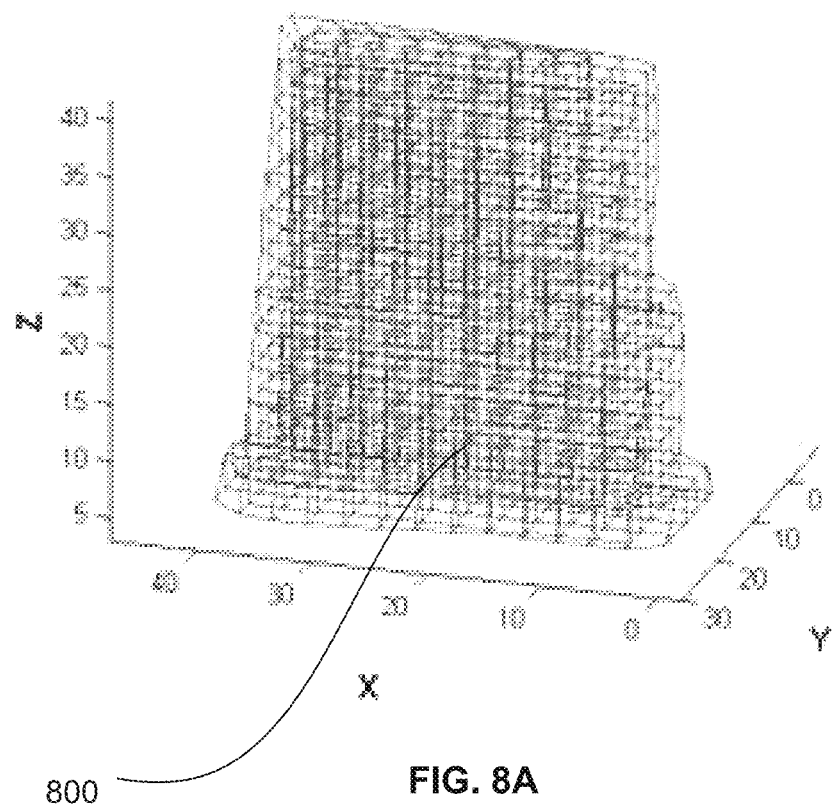
FIGS. 8A and 8B show an example of a periodic lattice structure generated using direct import of an STL file.
Figure 8B:
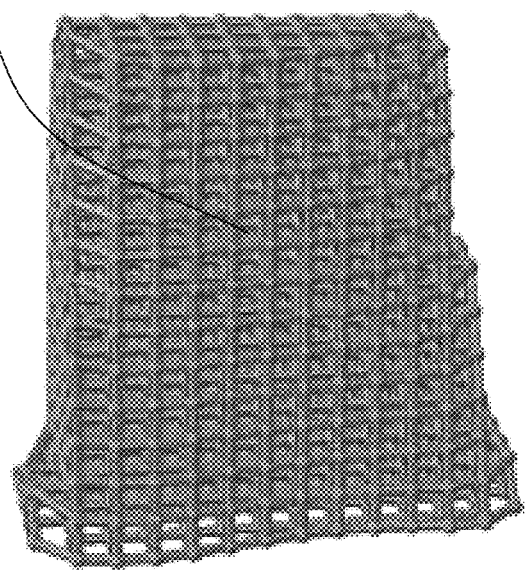
Figure 9D:
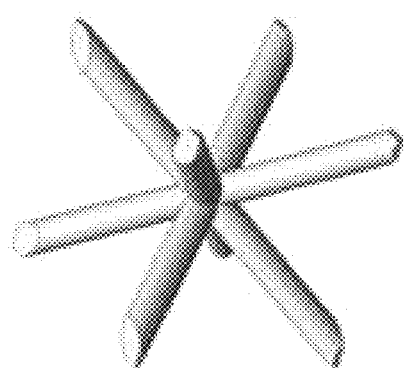
FIGS. 9A to 9D are exemplary lattice structure unit cells that may be used in a suitable periodic lattice structure.
Figure 9C:
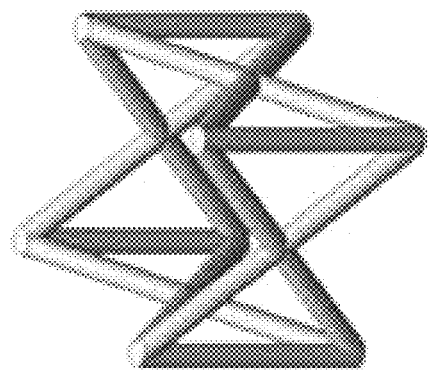
Figure 9B:
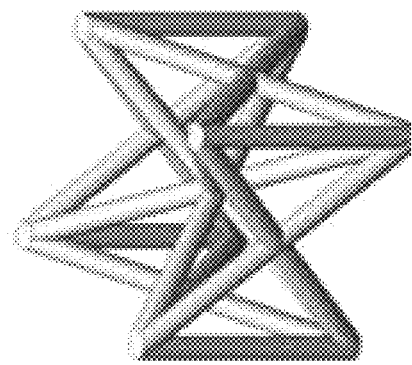
Figure 9A:
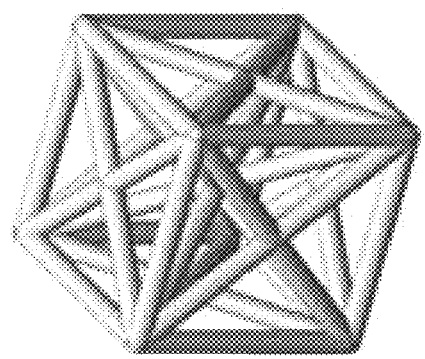

FIGS. 9A to 9D illustrate examples of unit cell types that can be applied to a periodic lattice structure 810 as shown in FIGS. 8A and 8B, for example. FIG. 9A shows a body centred cubic cell, FIG. 9B shows a face centred cubic cell with vertical struts, FIG. 9C shows a face and body centred cubic with vertical struts, and FIG. 9D shows face and body centred cubic with horizontal and vertical struts. The body centred cubic (BCC) type cells as shown in FIG. 9A are effectively employed in impact absorption applications due to their compliance. In contrast, the face centred cubic (FCC) type cells as shown in FIG. 9B are stiffer under compressive loading and accordingly useful for energy absorption. FCC type cells tend to be stronger when loaded in the Z direction, compared to the X and Y directions. This property makes them useful for load bearing implants since the resulting structure can exhibit increased stiffness in the loading direction, compared to other directions, enabling a reduction in the weight of the implant. The addition of horizontal elements to the unit cell, see for example the unit cell shown in FIG. 9D, increases the resistance of the structure to torsion and shear loading when compared with any of the other illustrated unit cell types.

Figure 10A:
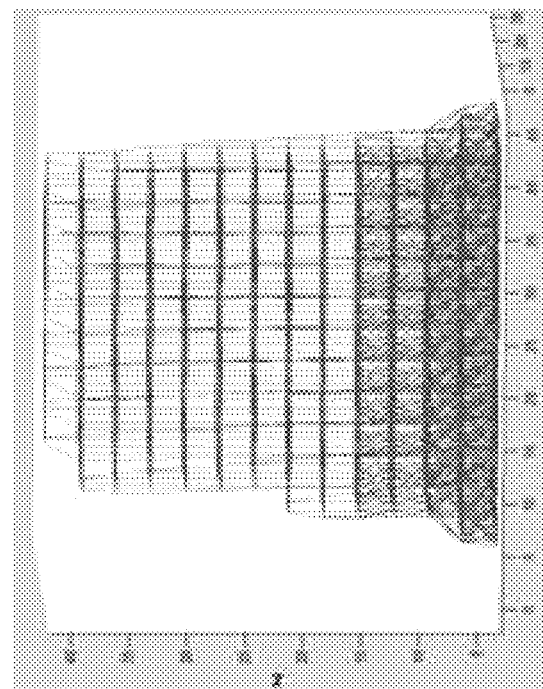
FIGS. 10A and 10B show the application of a functionally gradient structure to the lattice geometry.
Figure 10B:
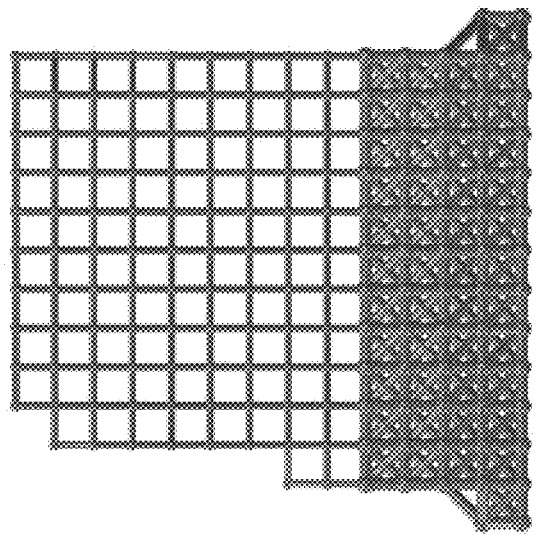

Referring now to FIGS. 10A and 10B, periodicity of the lattice structure also enables application of a functionally gradient structure to permit regulation of stiffness and/or enhance osseointegration (bone-ingrowth) by varying the density of the lattice structure near the bone/implant interface. FIG. 10B FIG shows a change in density of the lattice structure towards the implant interface by employing different unit cell types and a larger strut diameter when compared to the rest of the structure. Varying the density in this way near the implant interface enables bone ingrowth to be enhanced whilst at the same time maintaining a lightweight structure. The periodicity of the lattice structure provides precise control over the pore geometry and size. Accordingly, porosity of the structure will be easy to vary depending on whether enhancement of bone ingrowth or controlling stiffness of the implant is prioritised.

The customised orthopaedic implant is passed through an iterative process of its design involving topological optimisation to identify the optimal geometry to fill the space left by the removed tissue within the constraints provided by the anatomical features of the instant bone and the physique of the patient for whom the orthopaedic implant is being customised from step 260 to 264. If the structure does not meet the stress and deflection criterion, the geometry is modified and the structure is reassessed until optimal solution is achieved. Modification of geometry includes either reduction or increase in strut diameter.

Once the structure is optimised based on loading conditions at step 264, the three dimensional computer model of the proposed orthopaedic implant configuration is processed for additive manufacture at step 265. Typically this will involve conversion to a file format suitable for transmitting direct to a three dimensional printer or selective laser melting machine. The orthopaedic implant is then manufactured at step 270 using additive technology.

At step 275, the manufacturing process is monitored to ensure that in-situ process control measures are met. For example, such in-situ control measures might include a check of the build temperature and the manufactured geometry. If the control measures are not within acceptable limits at 280, then the proposed geometry and/or processing is modified at step 285. Suitable modifications might include adding support structure(s), altering the location or orientation of the part on the machine platform or changing the processing parameters.

If the in-situ control measures are within acceptable limits at 290, then the manufactured customised orthopaedic implant is subject to post processing at step 295, as required. Necessary post-processing may include but is not limited to mechanical and/or chemical processing to enhance the surface finish of the orthopaedic implant, removal of loose powder particles, and/or sterilisation of the customised orthopaedic implant in preparation for insertion into the patient.

Figure 11C:
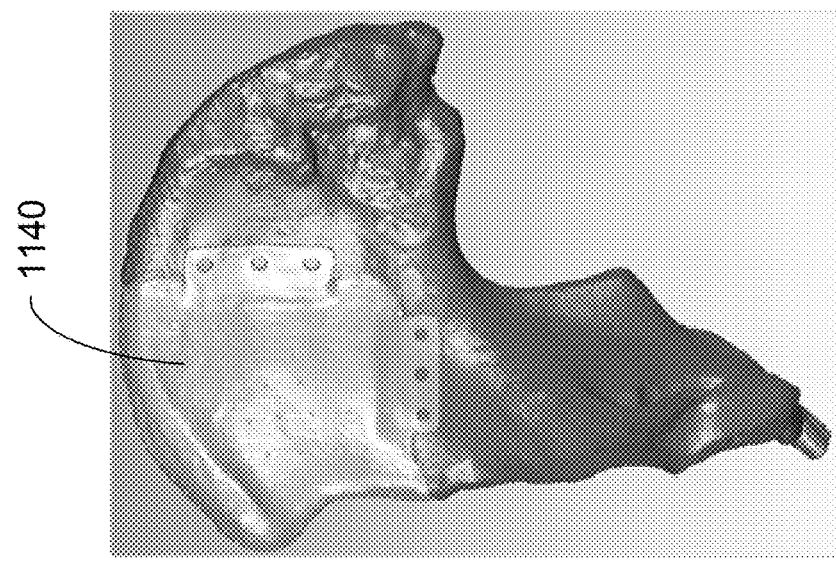
FIGS. 11A to 11C shows a series of schematics illustrating the customised orthopaedic implant inserted to replace the removed tissue.
Figure 11B:
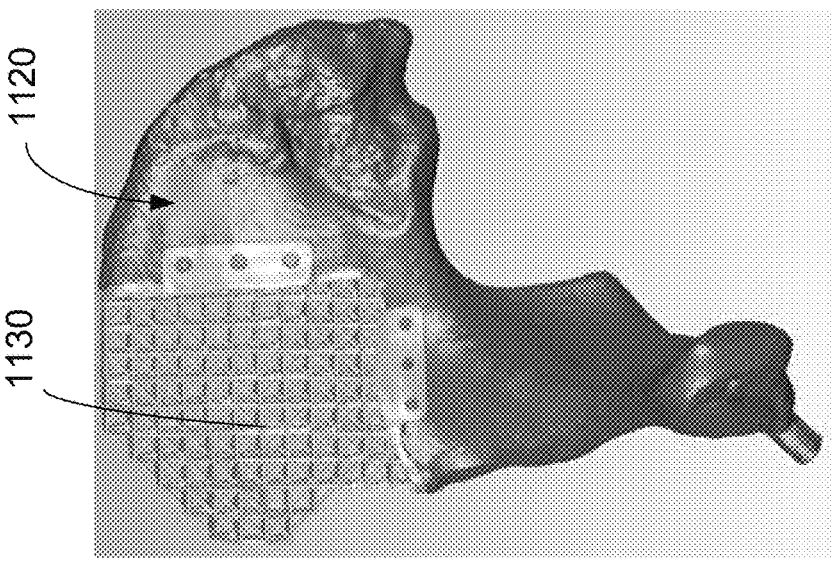
Figure 11A:
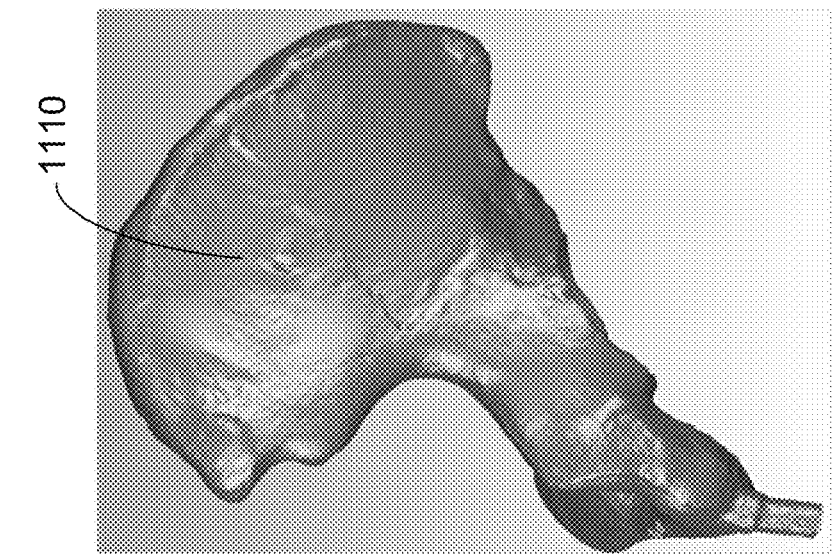

Finally, at step 298, the manufactured customised orthopaedic implant is delivered to the surgical team together with the relevant instructions for implantation. Referring now to FIGS. 11A to 11C, there is shown in FIG. 11A the unresected bone 1110, in FIG. 11B the resected bone 1120 is shown with the customised orthopaedic implant comprising a periodic lattice structure 1130 fixed thereto and in FIG. 11C a "skin" 1140 is provided over the orthopaedic implant 1130 which has optimally sized pores to enable flow of essential nutrients and promote bone osseointegration i.e. bone in-growth.

Various software and tools may be employed in implementing the method for producing a customised orthopaedic implant and particularly during the design process. These may include but are not limited to Mimics, Geomagic Studio/VX Elements with laser scanning, Solidworks, Abaqus, Matlab, Haptic Device/Freeform Modelling Plus and Magics/Autofab.

It is a particular advantage of the present invention, that not only is it possible to provide a customised orthopaedic implant specific to a patient and specific to a particular bone and the manner in which that bone has been resected, within a relatively short time frame. In particular, it appears that the customised orthopaedic implant could be produced in accordance with the method described herein within a period of time in which the patient is under anaesthesia. This suggests a significant improvement over method for producing customised orthopaedic implants which often require multiple surgical interventions before the orthopaedic implant can be inserted and hence result in a much longer recovery and rehabilitation time for the patient as well as often suboptimal outcomes owing to the difficulty of suitably customising the orthopaedic implant.

While the invention has been described in conjunction with a limited number of embodiments, it will be appreciated by those skilled in the art that many alternative, modifications and variations in light of the foregoing description are possible. Accordingly, the present invention is intended to embrace all such alternative, modifications and variations as may fall within the spirit and scope of the invention as disclosed.

The claims defining the invention are as follows:

1. A method for producing a customised orthopaedic implant formed of metal, the method comprising:
   a. scanning a bone, the bone being a diseased bone from which a region of bone that is diseased is to be resected to obtain a three dimensional digital image of an unresected volume of the diseased bone;
   b. resecting the region of bone that is diseased to leave a remaining volume of the bone from which the diseased region has been resected;
   c. scanning the remaining volume of bone after the region of bone that is diseased has been resected to obtain a corresponding three dimensional digital image of the remaining volume of bone;
   d. comparing the three dimensional digital image of the unresected volume of bone to the corresponding three dimensional digital image of the remaining volume of bone to estimate a volume of the region of bone that has been resected;
   e. using the estimate of the volume of the region of bone that has been resected to generate a three dimensional computer model that substantially conforms to a configuration of the volume of the region of bone that was resected and is optimised to substantially restore a biomechanical function of the bone on implantation of a customised orthopaedic implant corresponding to the optimised three dimensional computer model; and
   f. manufacturing the customised orthopaedic implant from the optimised three dimensional computer model, wherein the implant is configured for insertion into the region of the remaining bone from which the diseased region of bone has been resected in step b.
      wherein the customised orthopaedic implant is substantially comprised of a lattice-type geometry that has a periodic arrangement and that is conformal to the resected volume of bone, and
      wherein the optimisation to substantially restore the biomechanical function of the bone involves topological optimisation to provide the implant with an optimal conformal lattice-type geometry made in consideration of the anatomical function and of the properties of the bone type corresponding to the region of diseased bone that has been resected, together with patient-specific parameters and the anticipated loads to which the implant will be subjected during various typical activities and movements.

2. A method for producing a customised orthopaedic implant according to claim 1, wherein the topological optimisation involves consideration of patient-specific maximum stress and deflection to which the bone type which corresponds to the bone will be subjected during said various typical activities and movements.

3. A method for producing a customised orthopaedic implant according to claim 1, wherein the porosity of the lattice-type geometry is varied at a region of the implant configured to interface with the remaining volume of the bone so as to enhance bone ingrowth.

4. A method for producing a customised orthopaedic implant according to claim 1, wherein said manufacture is conducted using additive technology.

5. A method for producing a customised orthopaedic implant according to claim 4, wherein the additive technology involves selective laser melting.

6. A method for producing a customised orthopaedic implant according to claim 4, wherein prior to said manufacturing, the optimised three dimensional computer model is assessed for suitability for additive manufacture, and if required, modified to meet additive manufacture constraints.

7. A method for producing a customised orthopaedic implant according to claim 6, wherein said additive manufacture includes transmitting the three dimensional computer model to a three dimensional printer.

8. A method for producing a customised orthopaedic implant according to claim 1, wherein the step of scanning to obtain a three dimensional digital image in steps a. and/or c. comprises obtaining a plurality of two dimensional digital images from which the respective three dimensional image is constructed.

9. A method for producing a customised orthopaedic implant according to claim 1, wherein the diseased region of bone is affected by osteosarcoma.

10. A method for producing a customised orthopaedic implant according to claim 1, wherein steps a. to f. occur consecutively during a period of time in which a patient is under anaesthesia.

* * * * *